(12) United States Patent
Sherry et al.

(10) Patent No.: US 7,641,681 B2
(45) Date of Patent: Jan. 5, 2010

(54) LOW PROFILE STENT-GRAFT ATTACHMENT

(75) Inventors: John Sherry, Needham, MA (US); Fergus Quigley, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 302 days.

(21) Appl. No.: 11/025,826

(22) Filed: Dec. 28, 2004

(65) Prior Publication Data

US 2006/0142840 A1    Jun. 29, 2006

(51) Int. Cl.
    *A61F 2/06* (2006.01)
(52) U.S. Cl. ............ 623/1.13; 623/1.32; 623/1.44
(58) Field of Classification Search ............ 623/1.13, 623/1.39, 1.53, 1.15, 1.34, 1.42, 1.44–1.46, 623/1.32, 1.5; 87/5, 7, 13
    See application file for complete search history.

(56) References Cited

U.S. PATENT DOCUMENTS

| | | | |
|---|---|---|---|
| 3,719,210 | A | 3/1973 | Emerson et al. |
| 4,694,866 | A | 9/1987 | Kuo-Ching et al. |
| 5,123,917 | A | 6/1992 | Lee |
| 5,133,732 | A | 7/1992 | Wiktor |
| 5,282,824 | A | 2/1994 | Gianturco |
| 5,282,846 | A | 2/1994 | Schmitt |
| 5,314,472 | A | 5/1994 | Fontaine |
| 5,382,261 | A | 1/1995 | Palmaz |
| 5,383,925 | A | 1/1995 | Schmitt |
| 5,545,211 | A | 8/1996 | An et al. |
| 5,549,662 | A * | 8/1996 | Fordenbacher ............ 623/1.17 |
| 5,609,628 | A | 3/1997 | Keranen |
| 5,653,746 | A | 8/1997 | Schmitt |
| 5,700,285 | A | 12/1997 | Myers et al. |

(Continued)

FOREIGN PATENT DOCUMENTS

WO    WO 91/10766    7/1991

(Continued)

*Primary Examiner*—(Jackie) Tan-Uyen T. Ho
*Assistant Examiner*—Melissa Ryckman
(74) *Attorney, Agent, or Firm*—Vidas, Arrett & Steinkraus P.A.

(57) ABSTRACT

A low profile, implantable prosthesis includes (a) a tubular graft including opposed open ends and having yarns in a textile pattern to define a textile wall having a luminal surface and an exterior surface; and (b) a tubular, radially extensible member including a portion arranged in a closed zig-zag pattern, the pattern having a series of angled bends at proximal and distal ends thereof, and longitudinally extending members having opposed proximal and distal ends, the distal ends being disposed from the angled bends of the proximal end; the longitudinally extending members having a plurality of detents for securing the yarns within the textile pattern at one of the opposed open ends, wherein the yarns of the textile patterns are securably disposed to the detents. The detents may be holes, inwardly extending notches, outwardly extending protuberances, or combinations thereof in the longitudinally extending members. The textile pattern of the graft may be a braided textile pattern, a woven textile pattern, a knitted textile pattern, and combinations thereof. Desirably, the zig-zag portion of the radially extensible member is disposed beyond the open end of the graft. The radially extensible member may be a stent or may be an anchoring device for securing the prosthesis against the wall of a bodily lumen.

39 Claims, 6 Drawing Sheets

U.S. PATENT DOCUMENTS

| | | | |
|---|---|---|---|
| 5,720,776 A | 2/1998 | Chuter et al. | |
| 5,749,880 A | 5/1998 | Banas et al. | |
| 5,755,781 A | 5/1998 | Jayaraman | |
| 5,766,239 A * | 6/1998 | Cox | 606/194 |
| 5,800,526 A | 9/1998 | Anderson et al. | |
| 5,876,432 A | 3/1999 | Lau et al. | |
| 5,897,589 A | 4/1999 | Cottenceau et al. | |
| 5,925,075 A | 7/1999 | Myers et al. | |
| 5,948,017 A | 9/1999 | Taheri | |
| 6,074,416 A | 6/2000 | Berg et al. | |
| 6,077,296 A | 6/2000 | Shokoohi et al. | |
| 6,152,956 A | 11/2000 | Pierce | |
| 6,165,210 A | 12/2000 | Lau et al. | |
| 6,187,036 B1 | 2/2001 | Shaolian et al. | |
| 6,247,335 B1 | 6/2001 | Schaeberle et al. | |
| 6,273,909 B1 | 8/2001 | Kugler et al. | |
| 6,325,822 B1 | 12/2001 | Chouinard et al. | |
| 6,331,188 B1 | 12/2001 | Lau et al. | |
| 6,346,119 B1 | 2/2002 | Kuwahara et al. | |
| 6,482,227 B1 * | 11/2002 | Solovay | 623/1.13 |
| 6,517,570 B1 | 2/2003 | Lau et al. | |
| 6,540,773 B2 | 4/2003 | Dong | |
| 6,554,855 B1 | 4/2003 | Dong | |
| 6,596,023 B1 | 7/2003 | Nunez et al. | |
| 6,626,938 B1 | 9/2003 | Butaric et al. | |
| 6,640,590 B2 | 11/2003 | Thoman et al. | |
| 6,652,571 B1 | 11/2003 | White et al. | |
| 6,652,572 B2 | 11/2003 | Kugler et al. | |
| 6,740,115 B2 | 5/2004 | Lombardi et al. | |
| 2002/0035396 A1 | 3/2002 | Heath | |
| 2003/0139806 A1 | 7/2003 | Haverkost et al. | |
| 2003/0204241 A1 | 10/2003 | Dong | |
| 2004/0033364 A1 | 2/2004 | Spiridigliozzi et al. | |
| 2004/0044395 A1 | 3/2004 | Nelson | |
| 2004/0082989 A1 | 4/2004 | Cook et al. | |
| 2004/0111146 A1 | 6/2004 | McCullagh et al. | |

FOREIGN PATENT DOCUMENTS

| | | |
|---|---|---|
| WO | WO 01/26584 | 4/2001 |

* cited by examiner

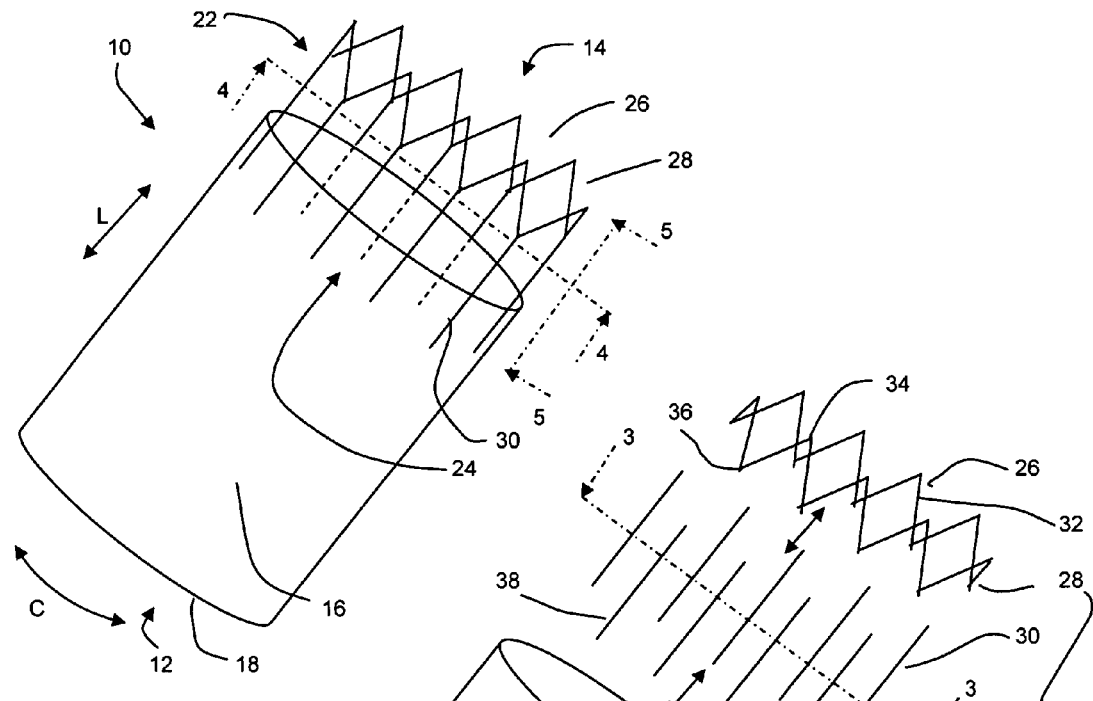
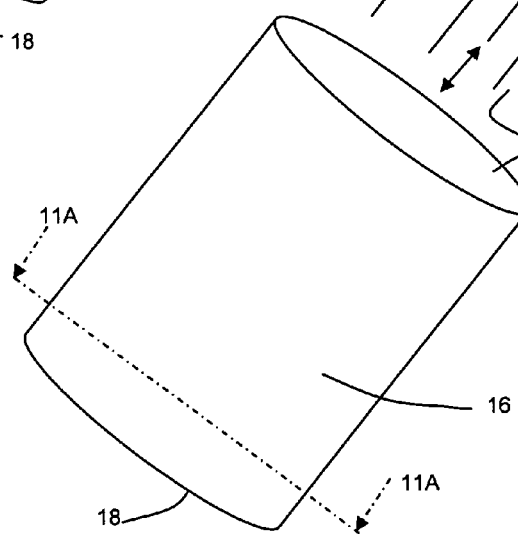
FIG. 1
FIG. 2

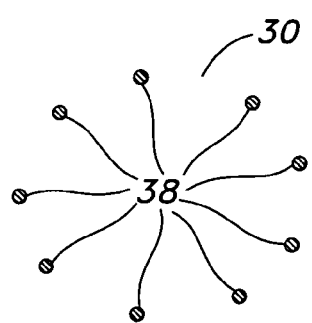
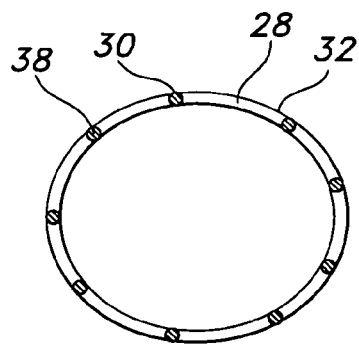
FIG. 3      FIG. 4
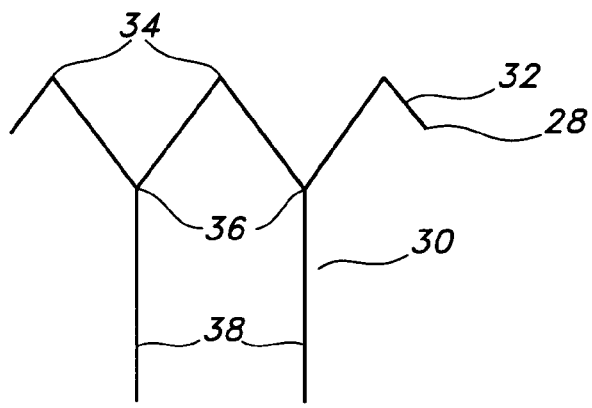
FIG. 5
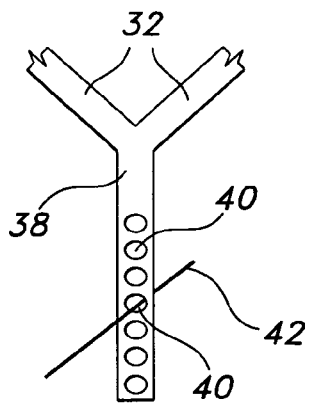 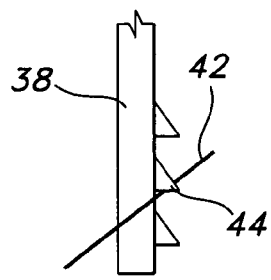 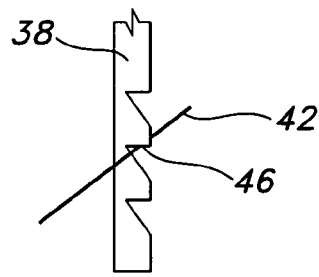
FIG. 6      FIG. 7      FIG. 8

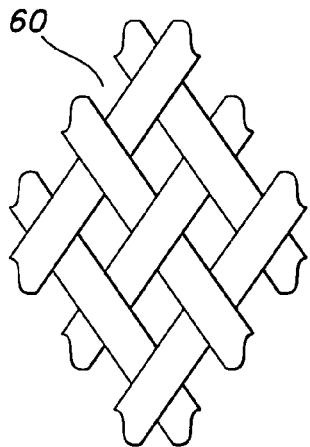
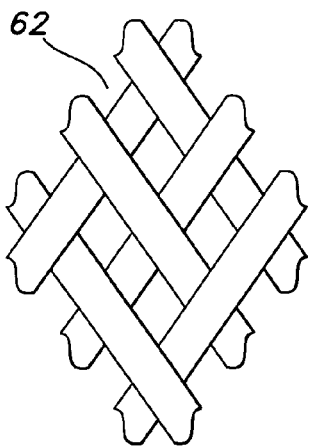
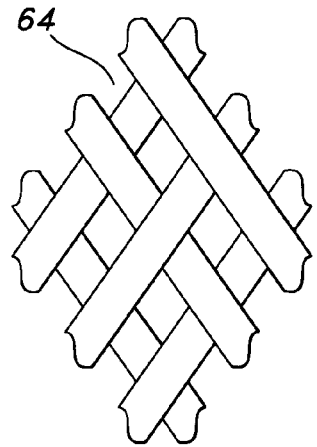
FIG. 12  FIG. 13  FIG. 14
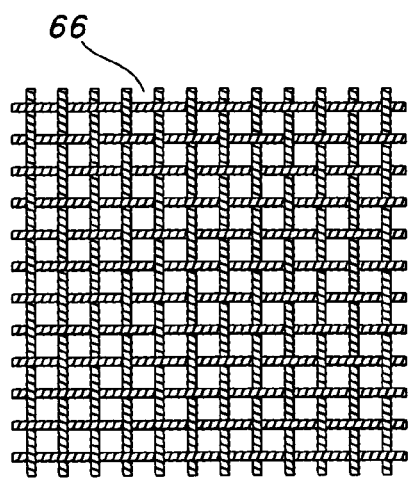
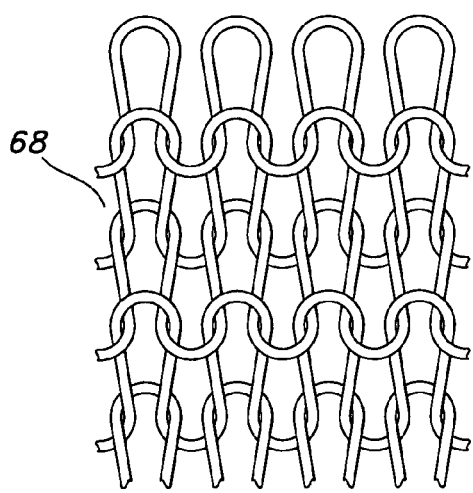
FIG. 15  FIG. 16

LOW PROFILE STENT-GRAFT ATTACHMENT

FIELD OF THE INVENTION

The present invention relates generally to an implantable prosthesis having a low-profile, a radially-extensible-member-graft attachment. More particularly, the present invention relates to a low-profile stent-graft attachment where the textile yarns forming the graft are inter-engaged with low-profile stent members.

BACKGROUND OF THE INVENTION

Implantable prostheses are commonly used in medical applications. One of the more common prosthetic structures is a tubular prosthesis which may be used as a vascular graft to replace or repair damaged or diseased blood vessels.

One form of a conventional tubular prosthesis specifically used for vascular grafts includes a textile tubular structure formed by weaving, knitting, braiding or any non-woven textile technique processing synthetic fibers into a tubular configuration. It is also well known to form a nontextile prosthesis, especially a tubular graft, from polymers such as polytetrafluoroethylene (PTFE). Such a nontextile tubular graft may be formed by stretching and expanding PTFE into a structure referred to as expanded polytetrafluoroethylene (ePTFE). Tubes formed of ePTFE exhibit certain beneficial properties as compared with textile prostheses. The expanded PTFE tube has a unique structure defined by nodes interconnected by fibrils. The node and fibril structure defines micropores which facilitate a desired degree of tissue ingrowth while remaining substantially fluid-tight. Tubes of ePTFE may be formed to be exceptionally thin and yet exhibit the requisite strength necessary to serve in the repair or replacement of a body lumen. The thinness of the ePTFE tube facilitates ease of implantation and deployment with minimal adverse impact on the body.

It is also known to use vascular grafts in conjunction with support structures. Such support structures typically come in the form of stents, which are formed of metal or polymeric materials generally formed in a tubular structure and are used to hold a vein or artery open. Stents are well known in the art and may be self-expanding or radially expandable by balloon expansion. Examples of stent/graft configurations known in the art can be seen in U.S. Pat. Nos. 5,700,285; 5,749,880; and 5,123,917, each of which are herein incorporated by reference. It is advantageous to use stent/graft configurations because the stent provides and ensures the patency of the prosthesis, while the vascular graft provides biocompatible properties in a vessel more suitable for blood to flow there through.

Various techniques have been discussed in the prior art for securing the stent and a graft to one and the other. For example, mechanical securement techniques have included the use of sutures, anchoring barbs, textile cuffs, and the like. These techniques increase the overall profile of the prosthesis and/or create stress points that may tear or otherwise deform the prosthesis. Further, bonding techniques have included adhesive and thermal bonding. The bonding techniques often result in limited bond strengths, especially in the longitudinal direction of the device. Often stents have been configured to have significant longitudinally traversing extents, in part to aid in stent-graft securement, but such extents also limit the overall profile of the device as these extents often limit the overall contractibility of the prosthesis.

It is therefore desirable to provide an implantable prosthesis, preferably in the form of a tubular vascular prosthesis, which achieves many of the above-stated benefits, such as low profile and enhanced stent/graft securement, without the resultant disadvantages associated therewith.

SUMMARY OF THE INVENTION

In one aspect of the present invention, a low profile, implantable prosthesis is provided. The prosthesis includes (a) a tubular graft comprising opposed open ends and having yarns in a textile pattern to define a textile wall having a luminal surface and an exterior surface; and (b) a tubular radially extensible member, such as a stent or a vessel anchoring device, comprising a portion arranged in a closed zig-zag pattern, the pattern having a series of angled bends at proximal and distal ends thereof, and longitudinally extending members having opposed proximal and distal ends. The distal ends are disposed from the angled bends of the proximal end. The longitudinally extending members have a plurality of detents for securing the yarns within the textile pattern at one of the opposed open ends. Advantageously, the yarns of the textile patterns are securably disposed to the detents. The detents may be holes, inwardly extending notches, outwardly extending protuberances, or combinations thereof in the longitudinally extending members. The textile pattern of the graft may be a braided textile pattern, a woven textile pattern, a knitted textile pattern, and combinations thereof. Desirably, the zigzag portion of the stent is disposed beyond the open end of the graft.

The longitudinally extending members are advantageously substantially longitudinally straight members, i.e., members that are parallel, are not inter-engaged with one and the other, and/or are not interconnected with one and the other except at angled bends of the zig-zag portion.

The prosthesis may further include a tubular layer of polymeric material securably disposed over portions of the luminal surface of the graft; a tubular layer of polymeric material securably disposed over portions of the exterior surface of the graft, and combinations thereof. Desirably, tubular layer is an extruded tube of the polymeric material, an extruded sheet of the polymeric material, a coating of the polymeric material, and combinations thereof.

In another aspect of the present invention, a method of reducing stent-graft profiles is provided. The method includes the steps of (a) providing a low profile stent member having a first portion with a lower profile than a second portion; the first portion having a plurality of longitudinally extending members with detents; (b) securably attaching yarns to the detents; and (c) inter-engaging the yarns in a textile pattern to form a tubular graft.

In a further aspect of the present invention, a method of making a prosthesis having a low profile radially-extensible-member/graft attachment is provided. The method includes the steps of (a) providing a tubular radially-extensible-member, such as a stent or a vessel anchoring device, comprising a portion arranged in a closed zig-zag pattern, the pattern having a series of angled bends at proximal and distal ends thereof, and longitudinally extending members having opposed proximal and distal ends, the distal ends being disposed from the angled bends of the proximal end; the longitudinally extending members having a plurality of detents; and (b) engaging yarns of a tubular textile graft with the detents to form a low-profile, radially-extensible-member/graft.

In another aspect of the present invention, an implantable prosthesis is provided. The prosthesis comprises (a) a tubular graft comprising opposed open ends and having yarns in a textile pattern to define a textile wall having a luminal surface and an exterior surface; and (b) a tubular, radially extensible member comprising a tubular portion arranged in an open-cell arrangement and longitudinally extending members having opposed proximal and distal ends, the distal ends being disposed from the tubular portion, the longitudinally extending members having a plurality of detents for securing the yarns within the textile pattern at one of the opposed open ends, wherein the yarns of the textile patterns are securably disposed to the detents.

BRIEF DESCRIPTION OF THE DRAWINGS

FIG. 1 is a perspective view of a prosthesis of the present invention depicting a graft and a radially extensible member securably disposed at one of the open ends of the graft.

FIG. 2 is an exploded, perspective view of the prosthesis of FIG. 1 further detailing different stent portion of the present invention.

FIG. 3 is a cross-sectional view of a portion of the prosthesis of FIG. 2 taken along the 3-3 axis.

FIG. 4 is a cross-sectional view of a portion of the prosthesis of FIG. 1 taken along the 4-4 axis.

FIG. 5 is a partial side elevational view of the radially extensible member of FIG. 1 taken along the 5-5 axis.

FIG. 6 is a partial elevational view of an elongate portion of the radially extensible member of FIG. 5 depicting holes for securing graft yarns to the radially extensible member.

FIG. 7 is a partial elevational view of an elongate portion of the radially extensible member of FIG. 5 depicting outwardly projecting detents for securing graft yarns to the radially extensible member.

FIG. 8 is a partial elevational view of an elongate portion of the radially extensible member of FIG. 5 depicting inwardly projecting detents for securing graft yarns to the radially extensible member.

FIG. 12 is a schematic of a diamond braid useful in the present invention.

FIG. 13 is a schematic of a regular braid useful in the present invention.

FIG. 14 is a schematic of a Hercules braid useful in the present invention.

FIG. 15 is a schematic of a regular weave useful in the present invention.

FIG. 16 is a schematic of a knit useful in the present invention.

DETAILED DESCRIPTION OF THE PREFERRED EMBODIMENT

Figure 9:
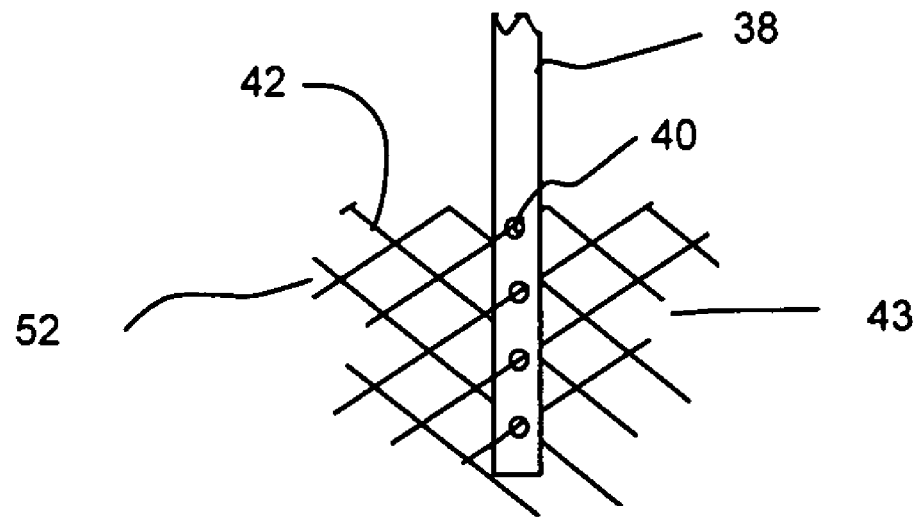
FIG. 9 is a side elevation view of the radially extensible member of FIG. 6 having braided textile yarns threaded through the holes of the elongate portion of the radially extensible member.

FIG. 1 is a perspective view of an implantable low profile prosthesis 10 of the present invention having a graft 16 and a radially extensible member 22, interrelated as shown. FIG. 2 is an exploded perspective view of the prosthesis 10 of FIG. 1 further depicting the interrelationship of the graft 16 and the radially extensible member 22. The prosthesis 10 is an elongate hollow, tubular device having opposed open ends 12, 14. The prosthesis 10 is characterized by a longitudinal axis or vector "L", which extends along the length of the prosthesis 10 between the opposed open ends 12, 14 in a non-traversing fashion. The prosthesis 10 is further characterized by a circumferential axis or vector "C" which extends radially from the longitudinal axis L, preferably in a perpendicular fashion. The prosthesis 10 includes a graft 16 having opposed open ends 18, 20 and a radially extensible member 22 having an opposed proximal end 24 and an opposed distal end 26. In FIGS. 1 and 2, the prosthesis 10 is depicted as having one radially extensible member 22 securably disposed at one of its open ends, i.e., graft end 20, but the invention is not so limited. A second radially extensible member (not shown) may be securably disposed at the other open end of the graft, i.e., graft end 18.

Radially extensible member 22 includes a first portion 28 and a second portion 30 securably disposed to one and the other. The radially extensible members 28 and 30 may be of unitary construction or may be separately formed members that are securably attached to one and the other. As depicted in FIGS. 1, 2 and 5, the first portion 28 of the radially-extensible-member 22 includes a wire 32 arranged in a closed zigzag fashion having a series of interconnected or undulating peaks 34 and valleys 36. The radially extensible member portion 28 may include a single wire 32 having its ends (not shown) securably joined to one and the other. Alternatively, radially extensible member 28 may include multiple wires (not shown) forming the closed zigzag arrangement. The second portion 30 of the radially extensible member 22 includes a plurality of elongate, longitudinally extending members 38.

Figure 18:
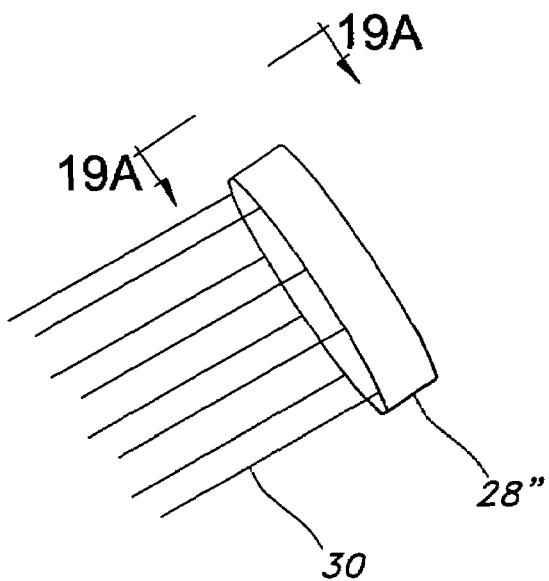
FIG. 18 is a perspective view of yet another alternate embodiment of the radially extensible member of FIG. 1.
Figure 19A:
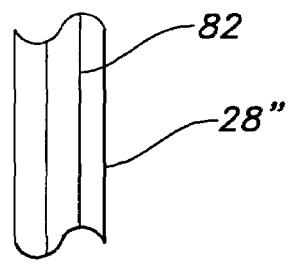
FIG. 19A is an exploded view of a portion of the radially extensible member of FIG. 18 taken along the 19A-19A axis showing an open arrangement thereat.
Figure 17:
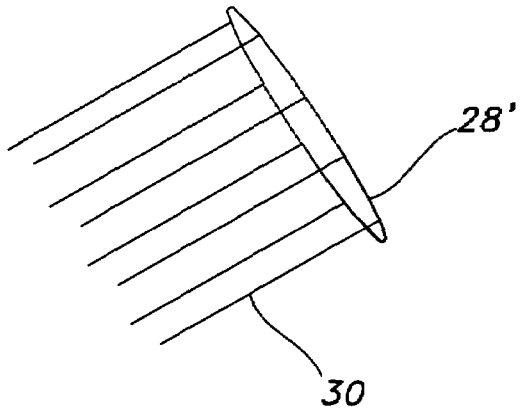
FIG. 17 is a perspective view of an alternate embodiment of the radially extensible member of FIG. 1.
Figure 19B:
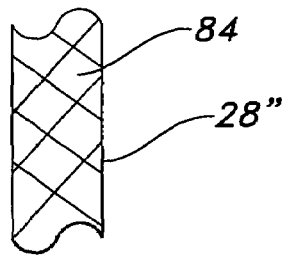
FIG. 19B is an exploded view of a portion of the radially extensible member of FIG. 18 showing an alternate open arrangement thereat.
Figure 19C:
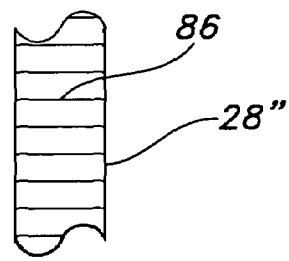
FIG. 19C is an exploded view of a portion of the radially extensible member of FIG. 18 showing another alternate open arrangement thereat.

The present invention, however, is not limited to a closed zigzag arrangement for the first portion 28 of the radially extensible member 22, and other arrangements may suitably be used. For example, as depicted in FIG. 17, the first portion 28' may comprise a single ring of an elongate wire. Further, as depicted in FIG. 18, the first portion 28" may be any suitable open-arrangement which provides outward radial force or radial compression resistance. As depicted in FIG. 19A, the open arrangement of the first portion 28" may be a series tubular rings or a coil of elongate wire 82. As depicted in FIG. 19B, the open arrangement of the first portion 28" may be a plurality of crossing wires 84, such as a braided pattern. As depicted in FIG. 19C, the open arrangement of the first portion 28" may be a plurality of longitudinally extending wires or even slotted members 86.

FIG. 3 is a cross-sectional view of the second radially extensible member 30 taken along the 3-3 axis of FIG. 2. As depicted in FIG. 3, the elongate members 38 are advantageously not connected to one and the other at proximal end 24 of the radially extensible member 22. Further, as depicted in FIG. 3, the elongate members 38 desirably do not contain longitudinally traversing extents at proximal end 24 of the radially extensible member 22. The lack of any inter-member stent connections and longitudinally traversing extents at the proximal location reduces the overall profile as compared to a radially extensible member having inter-member connections and/or longitudinally traversing extents. FIG. 4 is a cross-sectional view of the radially extensible member 22 taken along the 4-4 axis of FIG. 1. As depicted in FIG. 4, the radially extensible members 28 and 30 are substantially co-circular. The present invention, however, is not so limited. For example, portion 28 may have some outward flaring (not shown) to aid in securement of the stent portion 28 to a vessel wall, such as blood vessel wall.

FIG. 5 depicts side elevational view of a portion of the radially extensible member 22 taken along 5-5 axis of FIG. 1. Members 38, which form second radially extensible member 30, are depicted as longitudinally extending from each valley 36 of the zigzag portion 32 of the radially extensible member 22. The invention, however, is not so limited. For example, not every valley 36 of the radially extensible member 28 needs to have a member 38 extending therefrom.

FIG. 6 is a partial view of the elongate member 38. Elongate member 38 may include a detent 40 or a series of detents 40 for securing yarn 42 therethrough. The detents in FIG. 6 are depicted as holes or orifices 40. The yarn 42 may be threadingly looped through the holes 40. The present invention, however, is not limited to the use of holes 40 as detents for securing yarns 42 to elongate members 38. For example, as depicted in FIG. 7, outwardly extending or projecting detents or protuberances 44 may suitable be used detents for securing yarn 42. As depicted, in FIG. 8, inwardly projecting detents or notches 46 may suitably be used to secure yarns 42 as the detents.

The radially distensible member 22 may include, without limitation, self-expanding stents, balloon expandable stents, self-expanding anchoring devices and balloon expandable anchoring devices. The stents or devices may be capable of radially contracting as well. Self-expanding stents or devices include those that have a spring-like action which cause the stent or device to radially expand, or stents or devices which expand due to the memory properties of the stent material for a particular configuration at a certain temperature. Nitinol® is an example of a material which may be used as a self-expanding material for radially-extensible-member 22. Other materials are of course contemplated, such as stainless steel, cobalt-based alloy such as Elgiloy, platinum, gold, titanium, tantalum, niobium, and combinations thereof and other biocompatible materials, as well as polymeric materials. Further, the radially extensible member 22 or portions of the radially extensible member 22 may have an inner core of tantalum gold, platinum, iridium or combination of thereof and an outer member or layer of nitinol to provide a composite wire for improved radiocapicity or visibility. Further details of such composite wires may be found in U.S. Patent Application Publication 2002/0035396 A1, the contents of which is incorporated herein by reference. Preferably, the radially extensible member 22 is made from nitinol.

FIG. 9 depicts yarns 42 in a braided pattern 43 which forms textile wall 52 of the graft 16. Advantageously, the textile wall 16 is not sutured or stapled to the stent 22, but rather the yarns 42 that make up the textile pattern 43 are used for securement of the graft 16 to the elongate stent members 38. In other words, the yarns 42 that form the textile pattern 43 are integrated with the detents 40 of the radially extensible member 22 while maintaining the textile pattern 43 to form unitary or united, low profile stent-graft attachment. The textile pattern 43 is depicted as a braid textile pattern, but the present invention is not so limited and other textile patterns, such as a woven pattern or a knitted pattern may suitably be used.

Yarns 42 are desirably made from a textile material. The textile material may be formed from synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, pOlyethylenes, polyurethanes, polyolefins, polyvinyls, polymethylacetates, polyamides, naphthalane dicarboxylene derivatives, natural silk and polytetrafluoroethylenes. Moreover, at least one of the synthetic yarns may be a metallic yarn or a glass or ceramic yarn or fiber. Useful metallic yarns include those yarns made from or having stainless steel, platinum, gold, titanium, tantalum and Ni–Co–Cr-based alloy. The yarns may further comprise carbon, glass or ceramic fibers. Preferably, the yarns are made from thermoplastic materials including, but not limited to, polyesters, polypropylenes, polyethylenes, polyurethanes, polynaphthalenes, polytetrafluoroethylenes and the like. The yarns may be of the multifilament, monofilament or spun types. As is well known, the type and denier of the yarn chosen may be selected in a manner which forms a prosthesis and, more particularly, a vascular structure having desirable properties.

As depicted in FIG. 9, braiding of yarns 42 includes the interlacing of at least two yarn systems such that the paths of the yarns are diagonal to the fabric delivery direction, forming a tubular structure. Useful braids include, but are not limited to, a diamond braid having a 1/1 intersection repeat (i.e., braid 60 as depicted in FIG. 12), a regular braid having a 2/2 intersection repeat (i.e., braid 62 as depicted in FIG. 13), or a Hercules braid having a 3/3 intersection repeat (i.e., braid 64 as depicted in FIG. 14). U.S. Pat. No. 5,653,746, the content of which is incorporated herein by reference, further describes such braids. Moreover, a triaxial braid may also be used. A triaxial braid has at least one yarn that typically runs in the longitudinal direction or axial direction of the textile portion to limit yarn movement. The axial or longitudinal yarn is not interlaced or interwound with the other braid yarns, but is trapped between the different sets of yarns in the braided structure. Moreover, an interlocking three-dimensional braided structure or a multi-layered braided structure is also useful. A multi-layered braided structure is defined as a structure formed by braiding wherein the structure has a plurality of distinct and discrete layers.

Braiding machines, including circular braiding machines that form a braided textile over a mandrel, are useful with the practice of the present invention. An example of such a braiding machine is described in U.S. Pat. No. 6,652,571, the content of which is incorporated herein by reference. A braiding machine capable of forming the interlocked three-dimensional braid used to form the textile tube of the present invention is described in International Patent Publication No. WO 91/10766, which is incorporated herein by reference.

Generally, a braided structure is formed having a braid angle from about 30° to about 90° with respect to the longitudinal axis of the braided structure, desirably about 54.5° to about 75°. The yarns of the braid tend to seek equilibrium at a braid angle of about 54.5°, which is a neutral angle for tubular vessels under pressure. Thus, when the braid angle is larger than the neutral angle, when pressure is exerted from within, for example due to fluid flow, the yarns will tend to scissor and decrease the braid angle thereby elongating or stretching the braided structure in order to reach the neutral angle.

Useful weaves include, but are not limited to, simple or regular weaves (i.e., weave 66 as depicted in FIG. 15), basket weaves, twill weaves, satin weaves, velour weaves and the like. U.S. Pat. No. 5,653,746, the content of which is incorporated herein by reference, further describes such weaves. Desirably, the weaves are circular weaves, but the invention is not so limited. For example, the weave may be a flat woven tubular textile having the yarns inter-woven with the detents 40 of "unassembled" elongate members 38. The flat-woven, tubular graft with the unassembled elongate members 38 may then be placed on a tubular mandrel, and the elongate members 38 may then be connected to the zigzag portion 28 of the radially extensible member 22. Both flat weaving machines and circular weaving machines are known in the art. Circular weaving is a textile method where a tubular textile may be woven directly on a mandrel. A useful circular weaving machine in described in U.S. Pat. No. 3,719,210, the content of which is incorporated herein by reference.

Knitting involves the interlooping of one yarn system into vertical columns and horizontal rows of loops called wales and courses, respectively, with fabric coming out of the machine in the wale direction. Useful knits include, but are not limited to high stretch knits, locknit knits, which are also referred to as tricot or jersey knits (i.e., knit 68 as depicted in FIG. 16), reverse locknit knits, sharkskin knits, queenscord knits and velour knits. U.S. Pat. No. 5,653,746, the content of which is incorporated herein by reference, further describes useful knits. Useful high stretch, warp-knitted patterns include those with multiple patterns of diagonally shifting yarns, such as certain modified atlas knits which are described in U.S. Pat. No. 6,540,773, the contents of which are in incorporated herein by reference. Other useful high-stretch, warp knitted patterns include certain patterns with multiple needle underlap and one needle overlap, such as those patterns described in U.S. Pat. No. 6,554,855 and U.S. Patent Application Publication No. 2003/0204241 A1, the contents of which are incorporated herein by reference. Desirably, the knits are circular knits, but the invention is not so limited. For example, the knit may be a flat knitted tubular textile having the yarns inter-knitted with the detents 40 of "unassembled" elongate members 38. The flat-knitted, tubular graft with the unassembled elongate members 38 may then be placed on a tubular mandrel, and the elongate members 38 may then be connected to the zigzag portion 28 of the radially extensible member 22. Both flat knitting machines and circular knitting machines are known in the art. Circular knitting is a textile method where a tubular textile may be knitted directly on a mandrel. A useful circular weaving machine in described in U.S. Pat. No. 6,640,590, the content of which is incorporated herein by reference.

Figure 10:
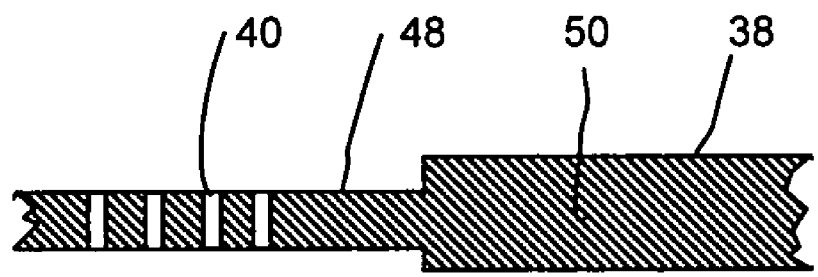
FIG. 10 is a cross-sectional of the elongate radially extensible member of FIG. 6 depicting a thinned portion of the radially extensible member.

As depicted in FIG. 10, the elongate 38 member may be thinned to reduce it overall profile. For example, portion 40, which contains the detents for securement of the yarns 42, is depicted as being thinner than portion 50. The present invention, however, is not so limited and either of the portions 40 or 50 could be the thinner end.

Figure 11A:
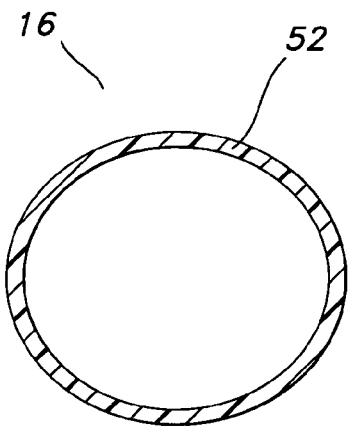
FIG. 11A is a cross-sectional of the graft of FIG. 2 taken along the 11A-11A axis depicting a textile graft wall.
Figure 11B:
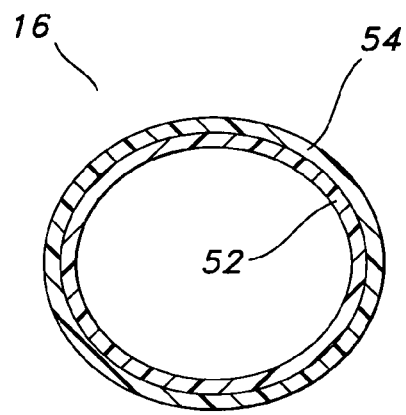
FIG. 11B is a cross-sectional of the graft of FIG. 11A showing a polymeric liner securably attached to the textile graft wall.
Figure 11C:
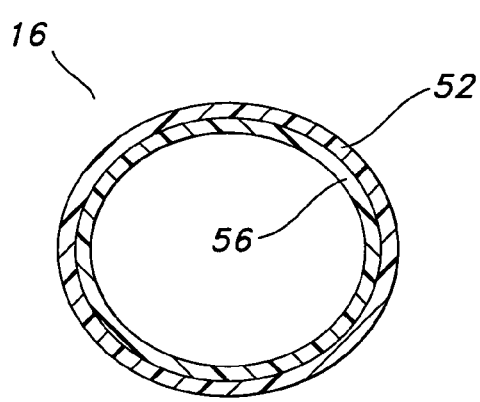
FIG. 11C is a cross-sectional of the graft of FIG. 11A showing a polymeric covering securably attached to the textile graft wall.
Figure 11D:
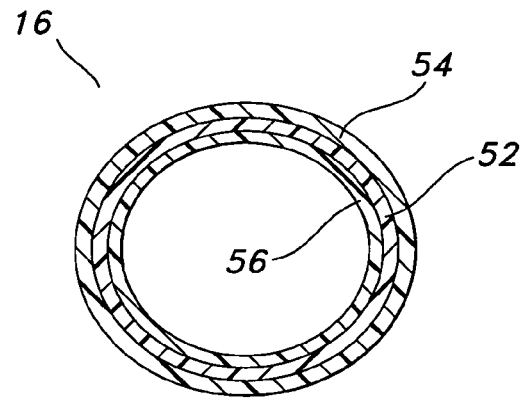
FIG. 11D is a cross-sectional of the graft of FIG. 11A showing a polymeric liner and a polymeric covering securably attached to the textile graft wall.

FIG. 11A is a cross-sectional view of a portion of the graft 16 of the stent-graft 10 of the present invention, taken along the 11A-11A axis. Graft 16 includes a graft wall 52. Graft wall 52 is depicted as a single layered wall in FIG. 11A. The yarns 42 are in a textile pattern to provide the textile wall 52. The present invention, however, is not so limited. For example, as depicted in FIG. 11B, an exterior layer 54 is shown being disposed over the exterior portions of textile wall 52. In FIG. 11B, an interior layer 56 is shown being disposed over the interior portions of textile wall 52. In FIG. 11D, an exterior layer 54 is shown being disposed over the exterior portions of textile wall 52 and an interior layer 56 is shown being disposed over the interior portions of textile wall 52.

The exterior layer 54 and the interior layer 56 prosthesis may be constructed of any suitable biocompatible materials, such as, but not limited to, polymeric polymers and materials, including fillers such as metals, carbon fibers, glass fibers or ceramics. Useful polymeric materials may include, for example, olefin polymers. Non-limiting examples of useful polymeric materials include polyethylene, polypropylene, polyvinyl chloride, polytetrafluoroethylene, including expanded polytetrafluoroethylene (ePTFE), fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, and copolymers and combinations thereof. The polymeric materials set forth above are intended to be exemplary only and should not be construed to limit in any way the types of materials which may be used in the present invention.

Desirably, the exterior layer 54 and the interior layer 56 are formed from polytetrafluoroethylene (PTFE) and/or expanded polytetrafluoroethylene (ePTFE). An ePTFE layer may be produced from the expansion of PTFE formed in a paste extrusion process. The PTFE extrusion may be expanded and sintered in a manner well known in the art to form ePTFE having a microporous structure defined by nodes interconnected by elongate fibrils. The distance between the nodes, referred to as the internodal distance, may be varied by the parameters employed during the expansion and sintering process. The resulting process of expansion and sintering yields pores within the structure of the ePTFE layer. The sizes of the pores are defined by the internodal distance of the ePTFE layer.

The textile wall 52 and the exterior layer 54 and/or the interior layer 56 may be adhesively bonded to form a composite prosthesis. The bonding agent may include various biocompatible, elastomeric bonding agents such as urethanes, styrene/isobutylene/styrene block copolymers (SIBS), silicones, and combinations thereof. Other similar materials are contemplated. Desirably, the bonding agent may include polycarbonate urethanes sold under the trade name CORETHANE®. This urethane is provided as an adhesive solution with preferably 7.5% Corethane, 2.5 W30, in dimethylacetamide (DMAc) solvent. Alternatively, the textile wall 52 and the exterior layer 54 and/or the interior layer 56 may be thermally bonded to form a composite prosthesis. Desirably, the textile wall 52 and the exterior layer 54 and/or the interior layer 56 are made from the same polymeric material, such as polytetrafluoroethylene, including expanded polytetrafluoroethylene, to facilitate the heat fusing of similar polymeric materials.

In one aspect of the present invention, an implantable prosthesis is provided. The prosthesis includes, but is not limited to, (a) a tubular graft comprising opposed open ends and having yarns in a textile pattern to define a textile wall having a luminal surface and an exterior surface; and (b) a tubular radially-extensible-member comprising a portion arranged in a closed zig-zag pattern, the pattern having a series of angled bends at proximal and distal ends thereof, and longitudinally extending members having opposed proximal and distal ends, the distal ends being disposed from the angled bends of the proximal end; the longitudinally extending members having a plurality of detents for securing the yarns within the textile pattern at one of the opposed open ends. Desirably, the yarns of the textile patterns are securably disposed to the detents.

The detents may be holes in the longitudinally extending members, inwardly extending notches in the longitudinally extending members, outwardly extending protuberances in the longitudinally extending members, and combinations thereof.

The textile pattern may be a braided textile pattern, a woven textile pattern, a knitted textile pattern, and combinations thereof. Desirably, the detents may be holes in the longitudinally extending members, the textile pattern is a braided textile pattern, and the yarns may be extended and/or inter-braided through the holes. Also desirably, the detents may be holes in the longitudinally extending members, the textile pattern is a woven textile pattern, and the yarns may be extended and/or interwoven through the holes. Further, the detents may be holes in the longitudinally extending members, the textile pattern is a knitted textile pattern, and the yarns may be extended and/or interknitted through the holes.

The zigzag portion of the radially-extensible-member is desirably disposed beyond the open end of the graft. The longitudinally extending members are also desirably substantially longitudinally straight members, are substantially parallel to one and the other, and/or are not interconnected to one and the other at any portion distal from the angled bends of the proximal end of the zig-zag portion. Inter-engagement includes, but is not limited to, one member crossing over the other member. Advantageously, the longitudinally extending members do not have any substantial longitudinally traversing extents or in other words do not have any substantial radially extending portions. Further, the proximal ends of longitudinally extending members may not have any substantial longitudinally traversing extents. Still further, the proximal ends of longitudinally extending members may be thinner in diameter than the distal ends of longitudinally extending members.

The yarns used in the prosthesis are biocompatible yarns, such as a polymeric material selected from the group consisting of polyesters, polypropylenes, polyethylenes, polyurethanes, polynaphthalenes, polytetrafluoroethylenes, and combinations thereof.

The prosthesis may further include a first tubular layer of polymeric material securably disposed over portions of the luminal surface of the graft and/or a second tubular layer of polymeric material securably disposed over portions of the exterior surface of the graft. The first tubular layer may be inverted to cover portions of both the luminal and exterior portions of the graft. The tubular layer may be selected from the group consisting of an extruded tube of the polymeric material, an extruded sheet of the polymeric material, a coating of the polymeric material, and combinations thereof. Desirably, the polymeric material is polytetrafluoroethylene, expanded polytetrafluoroethylene, and combinations thereof. Further details of polytetrafluoroethylene composite grafts useful with the practice of the present invention and methods for making the same may be found in commonly assigned patent application Ser. No. 11/025,571 titled "Low Profile, Durable, Reinforced ePTFE Composite Graft", filed on date herewith, the content of which is incorporated herein by reference.

The radially extensible member may be a stent, an anchoring device, and combinations thereof. As a stent, the longitudinally extending members and/or the zigzag portion secure the prosthesis against the wall of a bodily lumen and serve to keep the bodily lumen open. As an anchoring device, the zigzag portion secures the prosthesis against the wall of the bodily lumen.

A method of reducing stent-graft profiles according to the present invention includes, but is not limited to, the steps of (a) providing a low profile stent member having a first portion with a lower profile than a second portion; the first portion having a plurality of longitudinally extending members with detents; (b) securably attaching yarns to the detents; and (c) inter-engaging the yarns in a textile pattern to form a tubular graft. The textile pattern may be a braided textile pattern, a knitted textile pattern, a woven textile pattern, and combinations thereof. The step of inter-engaging the yarns may include inter-braiding the yarns, inter-knitting the yarns, inter-weaving the yarns, and combinations thereof, preferably, circular braiding the yarns, circular knitting the yarns, circular weaving the yarns, and combinations thereof.

A method of making the prosthesis having a low profile, stent- or anchoring-device/graft attachment according to the present invention includes, but is not limited to, the steps of (a) providing a tubular radially-extensible-member comprising a portion arranged in a closed zig-zag pattern, the pattern having a series of angled bends at proximal and distal ends thereof, and longitudinally extending members having opposed proximal and distal ends, the distal ends being disposed from the angled bends of the proximal end; the longitudinally extending members having a plurality of detents; (b) engaging yarns of a tubular textile graft to form a low-profile, radially-extensible-member/graft, such as a low-profile, stent-graft and/or a low-profile graft with a vessel anchoring device placing the stent over the mandrel; (e) engaging the yarns with the detents; and (f) forming a tubular textile graft having a textile pattern from the yarns over the mandrel. The method may further include some of the following steps of providing a tubular mandrel; providing a circular textile machine having a plurality of yarns; and forming a tubular textile graft having a textile pattern from the yarns over the mandrel.

The textile pattern may be selected from a braided textile pattern, a knitted textile pattern, a woven textile pattern, and combinations thereof. The step of engaging the yarns may include braiding the yarns, knitting the yarns, weaving the yarns, and combinations thereof.

The method of making the prosthesis having a low-profile stent-graft or low-profile, anchoring-device-graft attachment according to the present invention may further include the steps of (i) disposing a tubular, non-textile liner within the graft and securing the liner to the graft; or (ii) disposing a tubular, non-textile cover over the graft and securing the cover to the graft; or (iii) disposing a first tubular, non-textile liner with the graft, disposing a second tubular, non-textile cover over the graft and securing the liner and the cover to the graft. The step of securing the liner, and/or the cover to the graft may include adhesive bonding, chemical bonding, heat bonding, and combinations thereof. A cover and/or liner may be inverted to be disposed over a portion of the interior or luminal graft surface and a portion of the exterior graft surface. These steps may be performed with the use of a mandrel, where the graft and the liners or covers may be place over the mandrel.

In another aspect of the present invention, an implantable prosthesis is provided. The prosthesis comprises (a) a tubular graft comprising opposed open ends and having yarns in a textile pattern to define a textile wall having a luminal surface and an exterior surface; and (b) a tubular, radially extensible member comprising a tubular portion arranged in an open-cell arrangement and longitudinally extending members having opposed proximal and distal ends, the distal ends being disposed from the tubular portion, the longitudinally extending members having a plurality of detents for securing the yarns within the textile pattern at one of the opposed open ends, wherein the yarns of the textile patterns are securably disposed to the detents.

With any embodiment of the prosthesis 10 may be formed as a self-supporting prosthesis and usable to maintain patency of a bodily vessel, such as in the coronary vasculature, esophagus, trachea, colon, biliary tract, urinary tract, prostate, and brain. Also, prosthesis 10 may be treated with any of the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Various changes to the foregoing described and shown structures will now be evident to those skilled in the art. Accordingly, the particularly disclosed scope of the invention is set forth in the following claims.

What is claimed is:

1. An implantable prosthesis comprising:
   a tubular graft comprising opposed open ends and having yarns in a textile pattern to define a textile wall having a luminal surface and an exterior surface; and
   a tubular, radially extensible member comprising a tubular portion arranged in an open-cell arrangement and longitudinally extending members having opposed proximal and distal ends, said proximal ends of said longitudinally extending members extending from the tubular portion, said distal ends of said longitudinally extending members being distal from said tubular portion, said longitudinally extending members having a plurality of detents securing said yarns within said textile pattern at one of said opposed open ends,
   wherein said yarns of said textile patterns are securably engaged to said detents,
   wherein said tubular portion of said radially extendible member is disposed beyond one of said open ends of said graft, and
   wherein said longitudinally extending members are not in direct contact with to one another at any portion distal from said proximal ends of said longitudinally extending members extending from the tubular portion.

2. The prosthesis of claim 1, wherein said proximal ends of longitudinally extending members are thinner in diameter than said distal ends of longitudinally extending members.

3. The prosthesis of claim 1, wherein said yarns of said textile patterns are securably engaged to said detents without being sutured or stapled to said detents.

4. An implantable prosthesis comprising:
   a tubular graft comprising opposed open ends and having yarns in a textile pattern to define a textile wall having a luminal surface and an exterior surface; and
   a tubular, radially extensible member comprising a portion arranged in a closed zig-zag pattern, said zig-zag pattern having a series of angled bends at proximal and distal ends thereof, and longitudinally extending member having opposed proximal and distal ends, said proximal ends of said longitudinally extending members extending from the angled bends of said proximal end of zig-zag portion, said distal ends of said longitudinally extending members being distal from the angled bends of proximal end of said zig-zag portion; said longitudinally extending members having a plurality of detents securing said yarns within said textile pattern at one of said opposed open ends, wherein said yarns of said textile patterns are securably engaged to said detents, wherein said zigzag portion of said radially extendible member is disposed beyond one of said open ends of said graft, and
   wherein said longitudinally extending members are not in direct contact with to one another at any portion distal from the angled bends of said proximal ends of said zig-zag portion.

5. The prosthesis of claim 4, wherein said detents are holes in said longitudinally extending members.

6. The prosthesis of claim 4, wherein said textile pattern is selected from the group consisting of a braided textile pattern, a woven textile pattern, a knitted textile pattern, and combinations thereof.

7. The prosthesis of claim 4, wherein said detents are holes in said longitudinally extending members, said textile pattern is a braided textile pattern, and said yarns are extended through said holes.

8. The prosthesis of claim 4, wherein said proximal ends of longitudinally extending members are thinner in diameter than said distal ends of longitudinally extending members.

9. The prosthesis of claim 4, wherein said yarns of said textile patterns are securably engaged to said detents without being sutured or stapled to said detents.

10. An implantable prosthesis comprising:
    a tubular graft comprising opposed open ends and having yarns in a textile pattern to define a textile wall having a luminal surface and an exterior surface;
    a tubular, radially extensible member comprising a portion arranged in a closed zig-zag pattern, said zig-zag pattern having a series of angled bends at proximal and distal ends thereof, and longitudinally extending members having opposed proximal and distal ends, said proximal ends of said longitudinally extending members extending from the angled bends of said proximal end of said zig-zag portion, said distal ends of said longitudinally extending members being distal from the angled bends of said proximal end of said zig-zag portions; said longitudinally extending members having a plurality of detents securing said yarns within said textile pattern at one of said opposed open ends; and
    a tubular layer of polymeric material securably disposed over portions of said luminal surface of said graft,
    wherein said yarns of said textile patterns are securably engaged to said detents, wherein said longitudinally extending members are not in direct contact with to one another at any portion distal from the angled bends of said proximal end of said zig-zag portion, wherein said zigzag portion of said radially extendible member is disposed beyond one of said open ends of said graft, and wherein said tubular layer further includes an inverted portion securably disposed over portions of said exterior surface of said graft.

11. The prosthesis of claim 10, wherein said proximal ends of longitudinally extending members are thinner in diameter than said distal ends of longitudinally extending members.

12. The prosthesis of claim 10, wherein said yarns of said textile patterns are securably engaged to said detents without being sutured or stapled to said detents.

13. An implantable prosthesis comprising:

a tubular graft comprising opposed open ends and having yarns in a textile pattern to define a textile wall having a luminal surface and an exterior surface; and a tubular, radially extensible member comprising a portion arranged in a closed zig-zag pattern, said zig-zag pattern having a series of angled bends at proximal and distal ends thereof, and longitudinally extending members having opposed proximal and distal ends, said proximal ends of said longitudinally extending members extending from the angled bends of said proximal end of said zig-zag portion, said distal ends being distal from the angled bends of said proximal end of said zig-zag portion; said longitudinally extending members having a plurality of detents securing said yarns within said textile pattern at one said opposed open ends, wherein said longitudinally extending members are not in direct contact with to one another at any portion distal from the angled bends of said proximal end of said zig-zag portion, wherein said zigzag portion of said radially extendible member is disposed beyond one of the said open ends of said graft, wherein said yarns of said textile patterns are securably integrated with said detents, and wherein said detents are holes in said longitudinally extending members, said textile pattern is a braided textile pattern, and said yarns are extended through said holes.

14. The prosthesis of claim 13, wherein said detents are holes in said longitudinally extending members, said textile pattern is a woven textile pattern, and said yarns are extended through said holes.

15. The prosthesis of claim 13, wherein said detents are holes in said longitudinally extending members, said textile pattern is a knitted textile pattern, and said yarns are extended through said holes.

16. The prosthesis of claim 13, wherein said longitudinally extending members are substantially longitudinally straight members.

17. The prosthesis of claim 13, wherein said longitudinally extending members do not inter-engage one another.

18. The prosthesis of claim 13, wherein said longitudinally extending members are substantially parallel to one another.

19. The prosthesis of claim 13, wherein said proximal ends of longitudinally extending extending members are thinner in diameter than said distal ends of longitudinally extending members.

20. The prosthesis of claim 13, where said yarns are biocompatible yarns.

21. The prosthesis of claim 20, where said yarns are biocompatible yarns comprise a polymeric material selected from the group consisting of polyesters, polypropylenes, polyethylenes, polyurethanes, polynaphthalenes, polytetrafluoroethylenes, and combinations thereof.

22. The prosthesis of claim 13, further comprising a tubular layer of polymeric material securably disposed over portions of said luminal surface of said graft.

23. The prosthesis of claim 13, further comprising a tubular layer of polymeric material securably disposed over portions of said exterior surface of said graft.

24. The prosthesis of claim 13, further comprising: a first tubular layer of polymeric material securably disposed over portions of said luminal surface of said graft; and a second tubular layer of polymeric material securably disposed over portions of said exterior surface of said graft.

25. The prosthesis of claim 22, wherein said tubular layer further includes an inverted portion securably disposed over portions of said exterior surface of said graft.

26. The prosthesis of claim 22, wherein said tubular layer is selected from the group consisting of an extruded tube of said polymeric material, an extruded sheet of said polymeric material, a coating of said polymeric material, and combinations thereof.

27. The prosthesis of claim 23, wherein said tubular layer is selected from the group consisting of an extruded tube of said polymeric material, an extruded sheet of said polymeric material, a coating of said polymeric material, and combinations thereof.

28. The prosthesis of claim 24, wherein said first and second tubular layers are selected from the group consisting of an extruded tube of said polymeric material, an extruded sheet of said polymeric material, a coating of said polymeric material, and combinations thereof.

29. The prosthesis of claim 22, wherein said yarns are polytetrafluoroethylene yarns.

30. The prosthesis of claim 23, wherein said yarns are polytetrafluoroethylene yarns.

31. The prosthesis of claim 24, wherein said yarns are polytetrafluoroethylene yarns.

32. The prosthesis of claim 31, wherein said polymeric material selected from the group consisting of polytetrafluoroethylene, expanded polytetrafluoroethylene, and combinations thereof.

33. The prosthesis of claim 32, wherein said polymeric material selected from the group consisting of polytetrafluoroethylene, expanded polytetrafluoroethylene, and combinations thereof.

34. The prosthesis of claim 33, wherein said polymeric material selected from the group consisting of polytetrafluoroethylene, expanded polytetrafluoroethylene, and combinations thereof.

35. The prosthesis of claim 13, wherein said radially extensible member is a stent.

36. The prosthesis of claim 13, wherein said longitudinally extending members secure said prosthesis against a wall of a bodily lumen.

37. The prosthesis of claim 13, wherein said radially extensible member is an anchor device for securing said prosthesis against a wall of bodily lumen.

38. The prosthesis of claim 37, wherein said zig-zag portion is securable against a wall of a bodily lumen.

39. The prosthesis of claim 13, wherein said yarns of said textile patterns are securably integrated with said detents without sutured or stapled to said detents.

* * * * *

UNITED STATES PATENT AND TRADEMARK OFFICE
CERTIFICATE OF CORRECTION

PATENT NO. : 7,641,681 B2
APPLICATION NO. : 11/025826
DATED : January 5, 2010
INVENTOR(S) : Sherry et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this

Sixteenth Day of November, 2010

David J. Kappos
*Director of the United States Patent and Trademark Office*